US011511023B2

(12) United States Patent
Powell et al.

(10) Patent No.: US 11,511,023 B2
(45) Date of Patent: Nov. 29, 2022

(54) POSITION-ASSISTING DEVICE FOR EXPRESSING MILK

(71) Applicant: Arbor Grace, Inc., Detroit, MI (US)

(72) Inventors: Patrick Kenneth Powell, Detroit, MI (US); Marissa Gilbert, Harrison Township, MI (US); Eun-Jung Kim, Detroit, MI (US)

(73) Assignee: AG IP HOLDING LLC, Troy, MI (US)

( * ) Notice: Subject to any disclaimer, the term of this patent is extended or adjusted under 35 U.S.C. 154(b) by 288 days.

(21) Appl. No.: 16/844,697

(22) Filed: Apr. 9, 2020

(65) Prior Publication Data

US 2020/0324030 A1 Oct. 15, 2020

Related U.S. Application Data

(60) Provisional application No. 62/831,337, filed on Apr. 9, 2019.

(51) Int. Cl.
*A61M 1/06* (2006.01)

(52) U.S. Cl.
CPC .................................. *A61M 1/062* (2014.02)

(58) Field of Classification Search
CPC ...................... A61M 1/06–069; A47G 9/1045
See application file for complete search history.

(56) References Cited

U.S. PATENT DOCUMENTS

| 6,547,756 B1 * | 4/2003 | Greter ..................... A61M 1/06 604/74 |
| 9,930,977 B1 * | 4/2018 | Jennings ................ A47C 16/00 |
| 2011/0301533 A1 * | 12/2011 | Holshouser ........... A61M 1/062 604/74 |

FOREIGN PATENT DOCUMENTS

WO   WO-2020142240 A1 *  7/2020

* cited by examiner

*Primary Examiner* — Manuel A Mendez
*Assistant Examiner* — Courtney B Fredrickson
(74) *Attorney, Agent, or Firm* — Carlson, Gaskey & Olds, P.C.

(57) ABSTRACT

A position-assisting device for milk expression includes an upright body wedge pillow that defines a back side that has an armrest, a front user-engagement side that is sloped back, lateral sides, and a bottom side. The upright body wedge pillow has an upper head-rest section and an interior cavity that has a front face that opens to the front user-engagement side so as to be able to receive a woman's breasts for milk expression. There are breast pumps located in the interior cavity for milk expression.

17 Claims, 4 Drawing Sheets

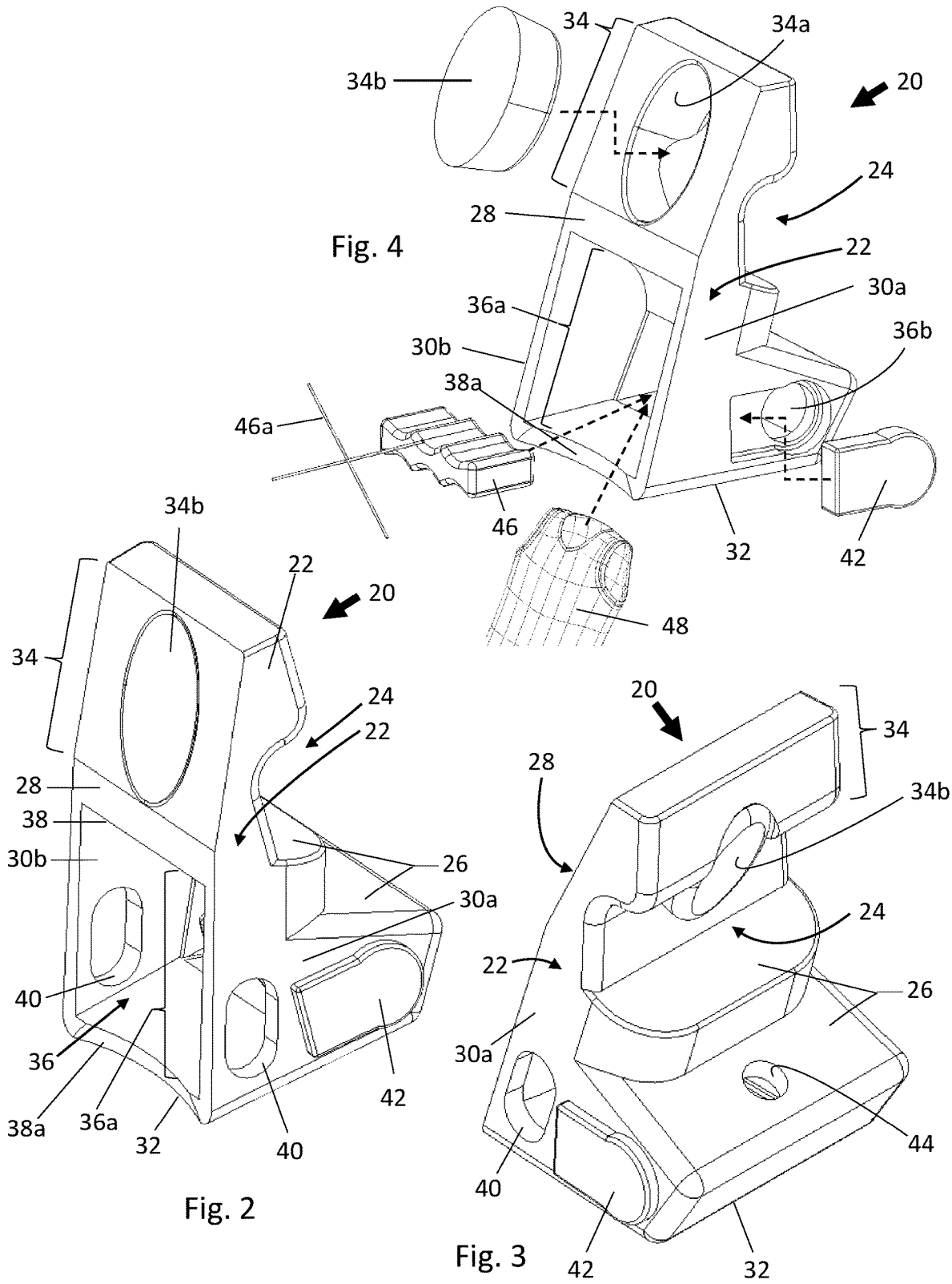

POSITION-ASSISTING DEVICE FOR EXPRESSING MILK

CROSS-REFERENCE TO RELATED APPLICATIONS

This application claims priority to U.S. Provisional Application No. 62/831,337 filed Apr. 9, 2019.

BACKGROUND

A breastfeeding mother is often busy with childcare, career, and home activities in addition to 4-6 hours per day spent breastfeeding and/or pumping milk for later use. With so many demands on time, it can be challenging to maintain a desired balance with health and sleep.

SUMMARY

A position-assisting device for milk expression according to an example of the present disclosure includes an upright body wedge pillow defining a back side having an armrest, a front user-engagement side that is sloped back, lateral sides, and a bottom side. The upright body wedge pillow has an upper head-rest section and an interior cavity having a front face opening to the front user-engagement side so as to be able to receive a woman's breasts for milk expression, and breast pumps located in the interior cavity.

A method of assisting in milk expression according to an example of the present disclosure includes using a position-assisting device to assist a woman in adopting a set posture for milk expression. The position-assisting device has an upright body wedge pillow that defines a back side that has an armrest, a front user-engagement side that is sloped back, lateral sides, and a bottom side. The upright body wedge pillow that has an upper head-rest section and an interior cavity that opens to the front user-engagement side so as to be able to receive a woman's breasts for milk expression, and breast pumps located in the interior cavity. Using includes receiving breasts of the woman into the interior cavity with the woman in a seated position and leaned forward against the front user-engagement side. The slope of the front user-engagement side positioning the woman in the set posture.

BRIEF DESCRIPTION OF THE DRAWINGS

The various features and advantages of the present disclosure will become apparent to those skilled in the art from the following detailed description. The drawings that accompany the detailed description can be briefly described as follows.

FIG. 2 illustrates an isolated view of a portion of a position-assisting device.

FIG. 3 illustrates front view of a position-assisting device.

FIG. 4 illustrates an expanded view of portions of a position-assisting device.

DETAILED DESCRIPTION

Figure 1A:
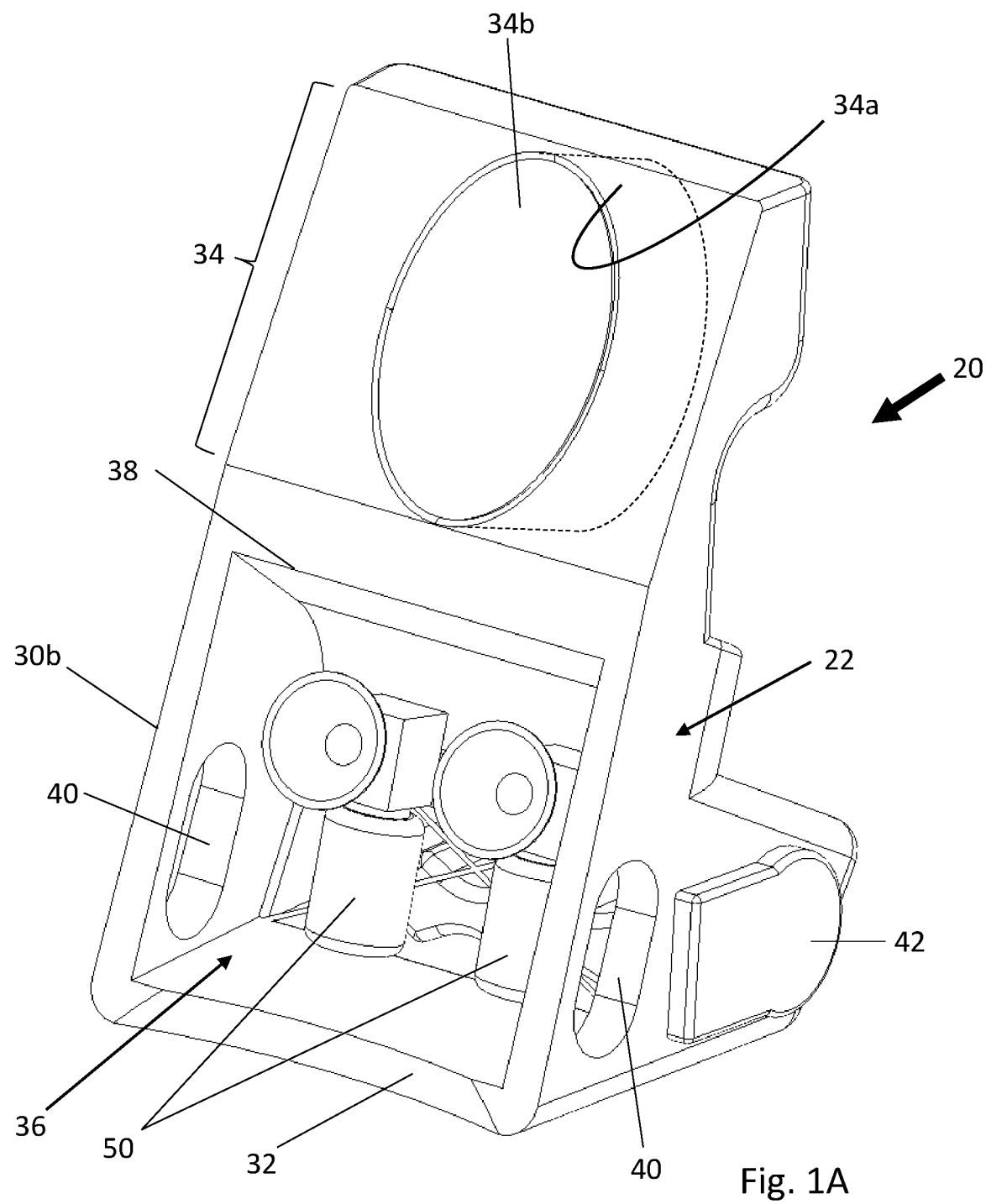
FIG. 1A illustrates an example position-assisting device for milk expression.
Figure 1B:
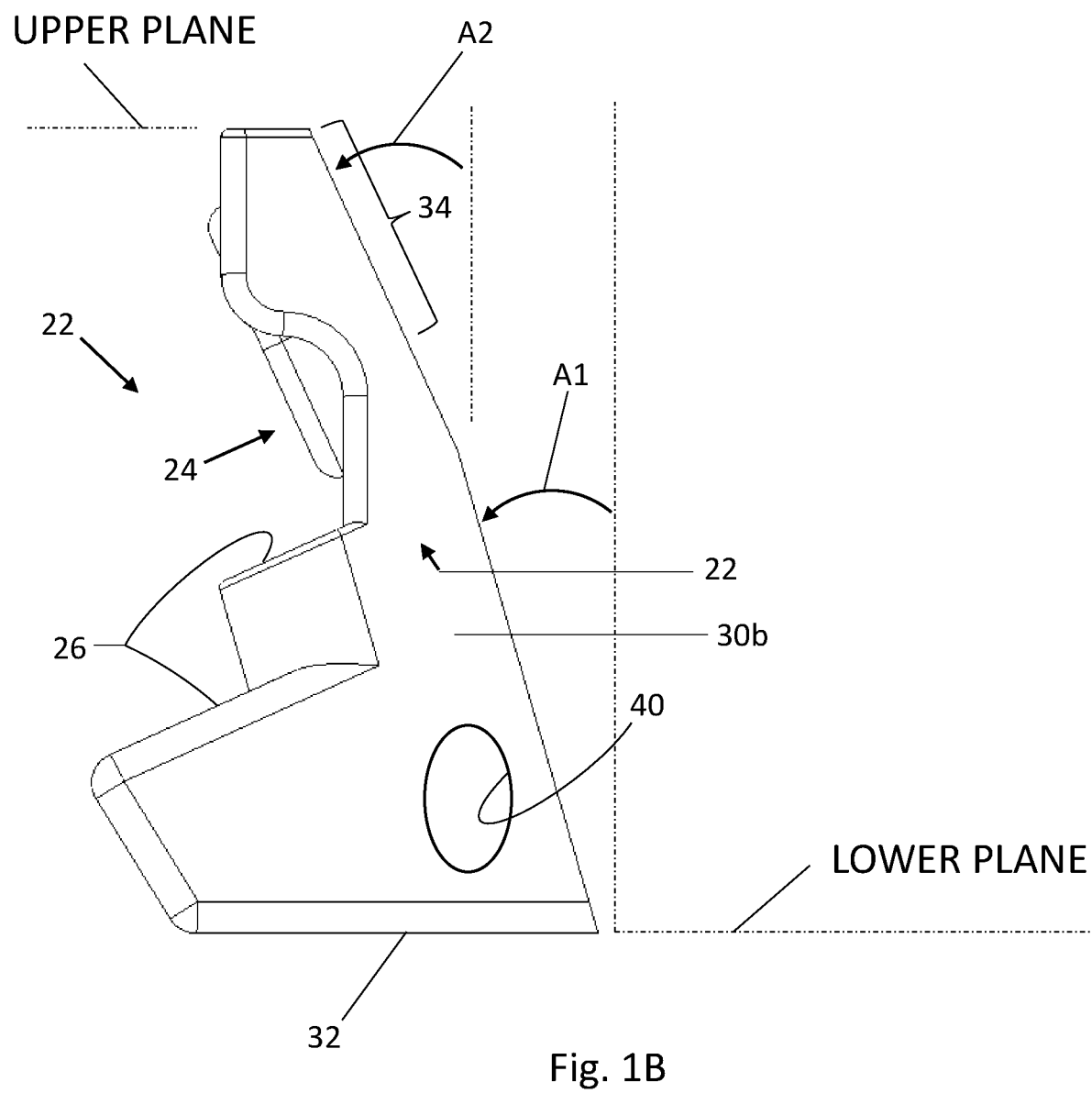
FIG. 1B illustrates a side view of a position-assisting device.

FIG. 1A schematically illustrates an example of a position-assisting device 20 for facilitating milk expression, and FIG. 1B illustrates a side view of the device 20. As will be appreciated from the present disclosure, the device 20 facilitates posture for milk expression, as well as providing comfort for rest.

The device 20 includes an upright body wedge pillow 22 (hereafter "pillow 22"), which is also shown in isolated views in FIG. 2 and FIG. 3. The term "upright" refers to the generally vertical functional orientation of the pillow 22. For example, the pillow 22 is made from foam or other soft material for providing comfort. As will be appreciated, portions of the pillow 22 may additionally be formed from rigid materials in order to provide supporting structure, and the pillow 22 may include a removable cover, indicated at 22a, for protection and aesthetics.

The pillow 22 generally defines a back side 24 that has at least one armrest 26, a front user-engagement side 28 that is sloped back (i.e., toward the back side 24), lateral sides 30a/30b, and a bottom side 32. The armrest or armrests 26 are generally slanted from horizontal so as to face outwardly from the device 20 and provide an angle that is comfortable for users. In the illustrated example, the device 20 includes two armrests 26, one being an upper armrest and the other being a lower armrest. The upper and lower armrests provide a user the ability to shift arm rest positions.

The front user-engagement side 28 is sloped at an angle (A1) relative to vertical. As will be described below, the angle assists the user in adopting a set posture for milk expression. For example, the angle A1 is from 10° to 30°. Angles above 30°, such as 45° or 55° are useful for milk expression but may increase chances of drowsiness.

The pillow 22 has an upper head-rest section 34 that serves as a place for a user to rest her head during use. The head-rest section 34 in the example shown is further sloped at an angle A2 relative to vertical, to allow the user's head to lie forward in a restful position. For example, the angle A2 is from 10° to 45°.

In the illustrated example, the head-rest section 34 includes a through-hole 34a with a removable pillow section 34b disposed therein. The removable pillow section 34b is complementary in shape to the through-hole 34a so as to be retained in the through-hole 34a until the user removes it. The removable pillow section 34b may be made of a different material and/or softer material that the immediately surrounding portion of the head-rest section 34.

The pillow 22 further includes an interior cavity 36. The interior cavity 36 is generally in the lower portion or half of the pillow 22 and has a front face 38 that opens to the front user-engagement side 28 so as to be able to receive a woman's breasts for milk expression. In that regard, the front face 38 may be of a height and a width to enable the woman to comfortably position her breasts into the interior cavity 36 without substantial pinching. The front face 38 is bounded on its lower side by an arced lip 38a, which also represents the anatomical curvature of the bottom side 32 of the pillow 22.

In this example, the interior cavity 36 includes a front cavity section 36a and a back cavity section 36b. The back cavity section 36b is recessed from the front cavity section 36a and is generally smaller in volume than the front cavity section 36a. The front cavity section 36a has the front face 38 that opens at the front user-engagement side 28.

The lateral sides 30a/30b of the pillow 22 include hand access openings 40 that open to the front cavity section 36a to provide user-access thereto. The openings 40 are in the lower portion of the pillow 22, such as in the lower one-third of the vertical height of the pillow 22, for ergonomic comfort of use. Toward the back side 24, the lateral side 30a also includes another opening in which a fan 42 is mounted. The fan 42 may be battery-powered and opens to the back cavity section 36b. As an example, the fan 42 is directionally controllable such that in a first direction the fan 42 draws ambient exterior air there through and into the back cavity section 36b, and in a second opposite direction the fan 42 expels air there through from the back cavity section 36b to the ambient surroundings. The pillow 22 may additionally include an air vent 44 through the armrest 26 into the back cavity section 36b. The functionality of the fan 42 and air flow will be described in additional detail below.

FIG. 4 illustrates an expanded view of portions of the device 20. The device 20 may additionally include a thermal pack 46 that fits into the back cavity section 36b. The thermal pack 46 can be retained in the back cavity section 36b by a lock 46a. For instance, the lock 46a is a retention cord that limits movement of the thermal pack 46.

For example, the thermal pack 46 is a cooling pack or a heating pack, such as a chilled or heated water-filled container. The thermal pack 46 is generally smaller than the volume of the back cavity section 36b and thus leaves storage space for other items, such as baby clothes 48.

As best shown in FIG. 1A, there are breast pumps 50 located in the interior cavity 36. The pumps 50 are in the front cavity section 36a, although a portion of the pumps may also be in the back cavity section 36b. The pumps 50 may be unsecured or free-floating in the cavity 36, secure in place to prevent movement, or semi-secured to allow limited movement for position adjustment. The pumps 50 have section cups or other features for engaging the breasts for milk expression. For example, the pumps 50 are electric pumps that are battery-powered. In that regard, the pumps 50 may be self-activating upon receiving a breast, or the pumps 50 may be activated by the user manually at the pumps 50 or by remote control.

Figure 5:
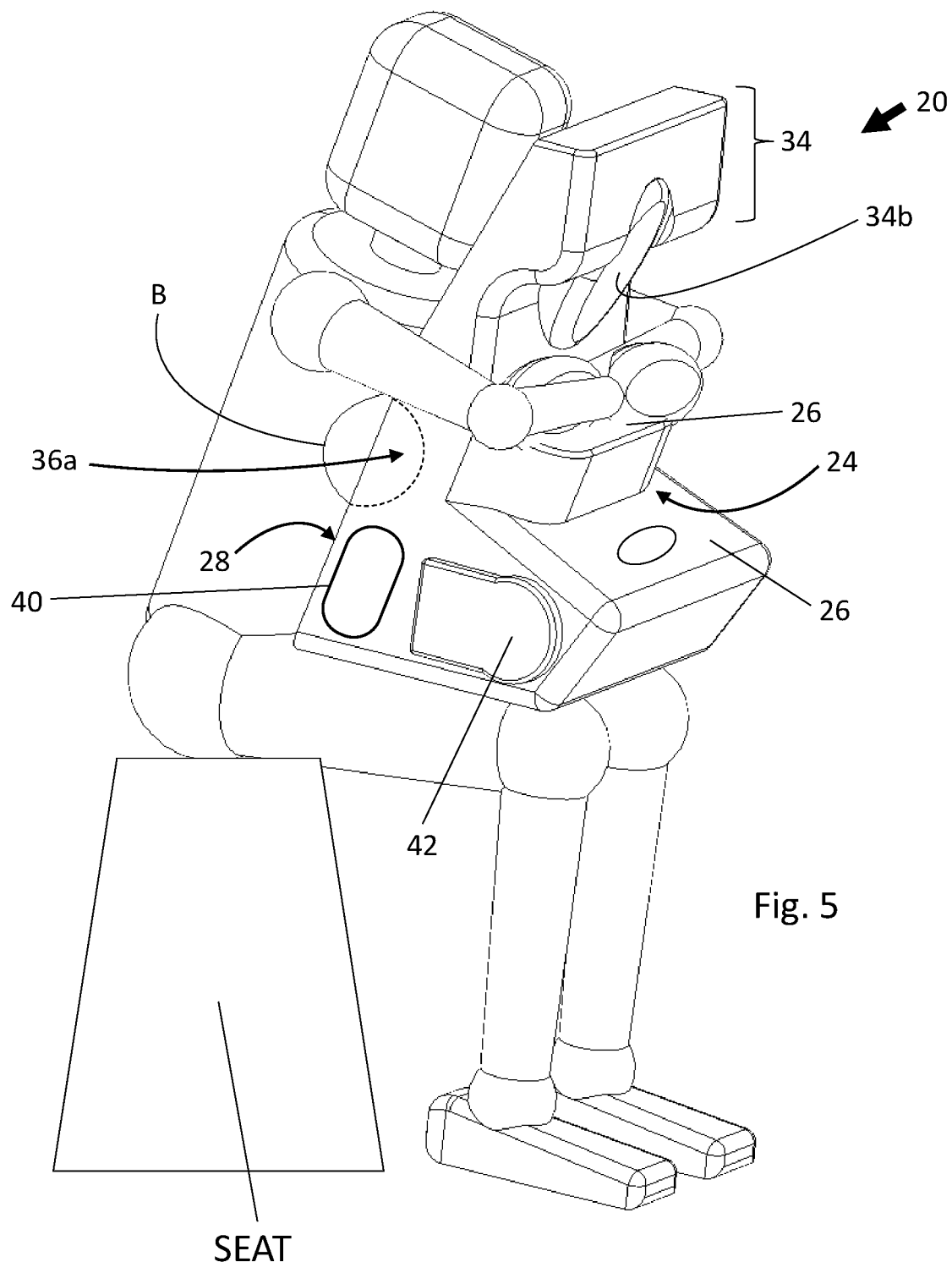
FIG. 5 illustrates a user using a position-assisting device.

FIG. 5 shows a woman using the device 20. In general, the woman is in a seated position and the device 20 is wedged in her lap so as to rest on her legs. In that regard, the bottom side 32 of the pillow 22 may be arced or anatomically shaped for additional comfort on the legs. In a hug-like manner, the woman's arms wrap around the device 20 and may rest on the armrest 26.

The angle A1 of the front user-engagement side 28 permits the woman to lean forward such that her breasts (B) are received into the front cavity section 36a of the interior cavity 36. The angle A1 is adapted to be shallow enough such that in the resulting leaned forward posture the woman's breasts suspend away from her body. Such a posture alleviates pressure on the breasts and facilitates opening milk ducts in the breasts to more freely pass milk to the exit nipple point. As a result, the milk may be expressed faster and there may be enhanced extraction of fat-infused milk. In further examples, the device 20 includes a frame or other support in which the pillow 22 is mounted. The frame is adjustable with regard to the posture angle, to permit the user to customize the angle at which she is leaned forward.

Without the device 20, such a leaned forward posture, although favorable for milk expression, would be difficult for a woman on her own to duplicate and maintain for the relevant amounts of time. However, the device 20 distributes the weight of the upper body onto the legs, thereby permitting the user to comfortably maintain the leaned forward posture for long periods of time. Moreover, the removable pillow section 34b may be used for additional comfort and rest. Alternatively, the user may remove the removable pillow section 34b and use the through-hole 34a as a view port in order to view a mobile device, talk with others, or keep watch over her baby, for example. In a further example, the device 20 may be outfitted with a harness, hooks, connectors, and/or recesses that permit other items to be attached, stored, or used with the device 20, such as but not limited to, a basinet for the baby.

Once in the set, leaned forward posture, the woman may position or adjust the breast pumps 50 through the hand access openings 40 for a proper and comfortable fit. Optionally, if the device 20 does not have the openings 40 or if the woman chooses, the pumps 50 may be adjusted via access through the front face 38. Once the pumps 50 are fit, the woman may activate the pumps 50 to begin milk expression. This may be accomplished by accessing the pumps 50 in the same manner as above and turning the pumps on or, if applicable, the pumps 50 and fan 42 may be activated and controlled by remote control.

The device 20 also facilitates assistance with breast health. Warm and cold temperatures on the breasts help to aid letdown and relieve breast engorgement. Letdown is the initiation of release of milk, and engorgement occurs when the breast tissues swell. The fan 42 and thermal pack 46 operate for temperature control in the device 20. For example, the fan 42 blows air over the thermal pack to heat or cool the air. The air then flows to the breasts to warm or cool the breasts before the air is discharged through the front face 38, openings 40, and/or air vent 44. In this regard, the fan 42 may have multiple speeds that the user can adjust in order to adjust the heating or cooling effect. Even without the thermal pack 46, the fan 42 can be used to blow air into the cavity 36, thereby pushing ambient surrounding air through the front face 38, openings 40, and/or air vent 44. The air flow circulation facilitates discharge of body-warmed air from the cavity 36 and replacement with cooler, ambient air. The fan 42 can also be used with or without the thermal pack 46 in the opposite direction to draw air out of the cavity 36, thereby pulling ambient surrounding air through the front face 38, openings 40, and/or air vent 44 into the cavity 36. The air flow circulation facilitates discharge of body-warmed air from the cavity 36 and replacement with cooler, ambient air.

The device 20 also facilitates enhanced milk expression. For example, the odor of the baby, such as odor from the body of the baby or odor left on the clothing of the baby, can trigger release of lactation-supporting hormones in the mother. In this regard, the cavity 36 can also accommodate used baby clothing, which releases the odor inside of the cavity 36. The fan 42 is operable to blow air through the cavity 36 and over the baby clothes therein. The odor becomes entrained in the air flow, which is then expelled through the front face 38, openings 40, and/or air vent 44 into the ambient surroundings where the mother can smell the scent while using the device 20.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from this disclosure. The scope of legal protection given to this disclosure can only be determined by studying the following claims.

What is claimed is:

1. A position-assisting device for milk expression comprising:
   an upright body wedge pillow defining a back side having an armrest, a front user-engagement side that is sloped back, lateral sides, and a bottom side, the upright body wedge pillow having an upper head-rest section and an interior cavity having a front face opening to the front user-engagement side so as to be able to receive a woman's breasts for milk expression, the interior cavity including a front cavity section that has the front face opening and a back cavity section that is smaller than the front cavity section in terms of volume; and
   breast pumps located in the interior cavity.

2. The position-assisting device as recited in claim 1, wherein the front user-engagement side includes a lower sloped section and an upper sloped section that are sloped at different angles relative to vertical.

3. The position-assisting device as recited in claim 1, further comprising a thermal pack in the back cavity section.

4. The position-assisting device as recited in claim 3, further comprising a lock retaining the thermal pack in the back cavity section.

5. The position-assisting device as recited in claim 1, wherein at least one of the lateral sides includes a fan that faces into the back cavity section.

6. The position-assisting device as recited in claim 1, wherein the back side includes an air vent connected to the back cavity section.

7. The position-assisting device as recited in claim 1, further comprising a fan in communication with the back cavity section.

8. The position-assisting device as recited in claim 1, wherein the upper head-rest section includes a through-hole window.

9. The position-assisting device as recited in claim 8, wherein the upper head-rest section includes a removable pillow section disposed in the through-hole window and complementary in shape to the through-hole window.

10. The position-assisting device as recited in claim 1, wherein the front face opening has an arced lip.

11. The position-assisting device as recited in claim 1, wherein the upright body wedge pillow is made of foam.

12. The position-assisting device as recited in claim 1, wherein each of the lateral sides has a hand access opening.

13. The position-assisting device as recited in claim 1, wherein the upright body wedge pillow includes a removable cover.

14. A method of assisting in milk expression, the method comprising:
   using a position-assisting device to assist a woman in adopting a set posture for milk expression,
   the position-assisting device includes
      an upright body wedge pillow that defines a back side that has an armrest, a front user-engagement side that is sloped back, lateral sides, and a bottom side, the upright body wedge pillow having an upper head-rest section and an interior cavity that opens to the front user-engagement side so as to be able to receive a woman's breasts for milk expression, and
      breast pumps located in the interior cavity;
   the using includes receiving breasts of the woman into the interior cavity with the woman in a seated position and leaned forward against the front user-engagement side, the slope of the front user-engagement side positioning the woman in the set posture; and
   circulating air through the interior cavity during use via a fan in the position-assisting device.

15. The method as recited in claim 14, further comprising a thermal pack in the interior cavity, and the fan moves the air over the thermal pack during use.

16. The method as recited in claim 14, further comprising attaching at least one of the breast pumps to one of the breasts and activating the at least one breast pump in order to express milk.

17. A position-assisting device for milk expression comprising:
   an upright body wedge pillow defining a back side having an armrest, a front user-engagement side that is sloped back, lateral sides, and a bottom side, the upright body wedge pillow having an upper head-rest section and an interior cavity having a front face opening to the front user-engagement side so as to be able to receive a woman's breasts for milk expression, the upper head-rest section including a through-hole window; and
   breast pumps located in the interior cavity.

* * * * *